United States Patent [19]

Cerwin et al.

[11] Patent Number: 5,052,551
[45] Date of Patent: Oct. 1, 1991

[54] OVAL WRAP SUTURE PACKAGE WITH UNEQUAL END RADII

[75] Inventors: Robert J. Cerwin, Pipersville, Pa.; Anthony Esteves, Somerville, N.J.; Marvin Alpern, Glen Ridge, N.J.; Robert A. Daniele; Robert J. Gibbs, both of Flemington, N.J.

[73] Assignee: Ethicon, Inc., Somerville, N.J.

[21] Appl. No.: 648,708

[22] Filed: Jan. 31, 1991

[51] Int. Cl.⁵ .................... A61B 17/06; B65D 85/00
[52] U.S. Cl. .................... 206/63.3; 206/524.1; 206/339; 206/380
[58] Field of Search .................... 206/63.3, 524.1, 339, 206/380

[56] References Cited

U.S. PATENT DOCUMENTS 4,961,498  10/1990  Kalinski et al. ............. 206/63.3 X
4,967,902  11/1990  Sobel et al. ................. 206/63.3

Primary Examiner—William I. Price
Attorney, Agent, or Firm—James Riesenfeld

[57] ABSTRACT

An oval wrap suture package that permits sutures to be dispensed with less likelihood of suture binding is provided. In one embodiment, the package has a suture winding channel with semicircular end sections whose radii are unequal. In another embodiment of the invention, the suture package is molded from a polymeric resin mixture that includes at least 4% oleamide.

13 Claims, 2 Drawing Sheets

OVAL WRAP SUTURE PACKAGE WITH UNEQUAL END RADII

BACKGROUND OF THE INVENTION

1. Field of the Invention

This invention relates to packages for holding needles and attached sutures; in particular, packages that permit a needle and suture to be removed without any suture binding.

2. Description of the Related Art

In the packaging of surgical needles, including surgical needles to which there are attached sutures, it is important that the needle and its attached suture be easily removable from the package in one smooth motion. When the needle is grasped by a forceps and pulled, the needle should easily release from the package, and the suture should withdraw from the package smoothly, without binding or snagging in the package, and without becoming entangled. Also, suture materials, particularly monofilaments such as catgut, polydioxanone and the like, especially the heavier deniers, are known to take a set during storage; i.e., they tend to have a "memory" causing them to retain the shape of their position in the package after removal from the package. Hence, the package should be designed to eliminate any tight bends or curves required in order to package the suture.

It is further desirable for suture packages to be economical to manufacture in volume quantities. A manufacturing process directed toward this end is one in which the suture package is formed of two interlocking molded, stamped, or thermoformed polymeric members. Such a process permits the formation of projections useful for winding and capturing the suture in channels designed for that purpose. In addition, the fine tolerances necessary in the execution of a precision design can be maintained.

Oval wrap suture packages have been disclosed in U.S. Pat. No. 4,961,498, issued Oct. 9, 1990 to Kalinski et al.; and U.S. Pat. No. 4,967,902, issued Nov. 6, 1990 to Sobel et al. These packages include a structure to hold (or "park") a needle and an oval ("racetrack-shaped") channel for retaining a suture that is attached to the needle. Although the two-piece package of Kalinski et al. and the one-piece package of Sobel et al. permit needled sutures to be removed from their packages with only infrequent snagging of the suture, the inconvenience and cost (both time and money) of snagged sutures provide an incentive to fabricate packages that minimize the likelihood of a suture being impeded as it is removed from its package.

SUMMARY OF THE INVENTION

In accordance with the present invention, a suture package that defines an oval suture winding channel comprises two substantially straight opposing sections connected by opposing first and second semicircular end sections, in which the first semicircular section has a larger radius than the second semicircular section. It is important to understand that the end sections need not be "semicircular" in the mathematical sense. Thus, an end section may comprise a curved arc that does not trace out a section of a circle or it may comprise about half of a many-sided polygon (e.g., hexagon, octagon, etc.). Similarly, the "radius" of an end section that is not a circular section is understood to be a measure—corresponding to the radius of a circle—of the curvature of the arc or the size of the polygon. For purposes of this specification and the appended claims, it is these broader definitions that are intended when the terms "semicircular" and "radius" are used.

A package having unequal radii for the arcs at the two ends of the oval reduces the likelihood that a suture will snag as it is being removed. At the same time, there is little or no need to enlarge the outer dimensions of the package. This is important, because certain "standard" package dimensions have been developed, and there would be great inconvenience caused to suture manufacturers and/or their customers if these dimensions had to be changed.

In another embodiment, the present invention provides a suture package that defines an oval suture winding and that is molded from a polymeric resin mixture, at least 4% of which comprises an oleamide. A suture package molded from such a resin mixture permits smoother dispensing of sutures, with a reduced likelihood of suture snagging.

DETAILED DESCRIPTION OF THE INVENTION

Figure 1:
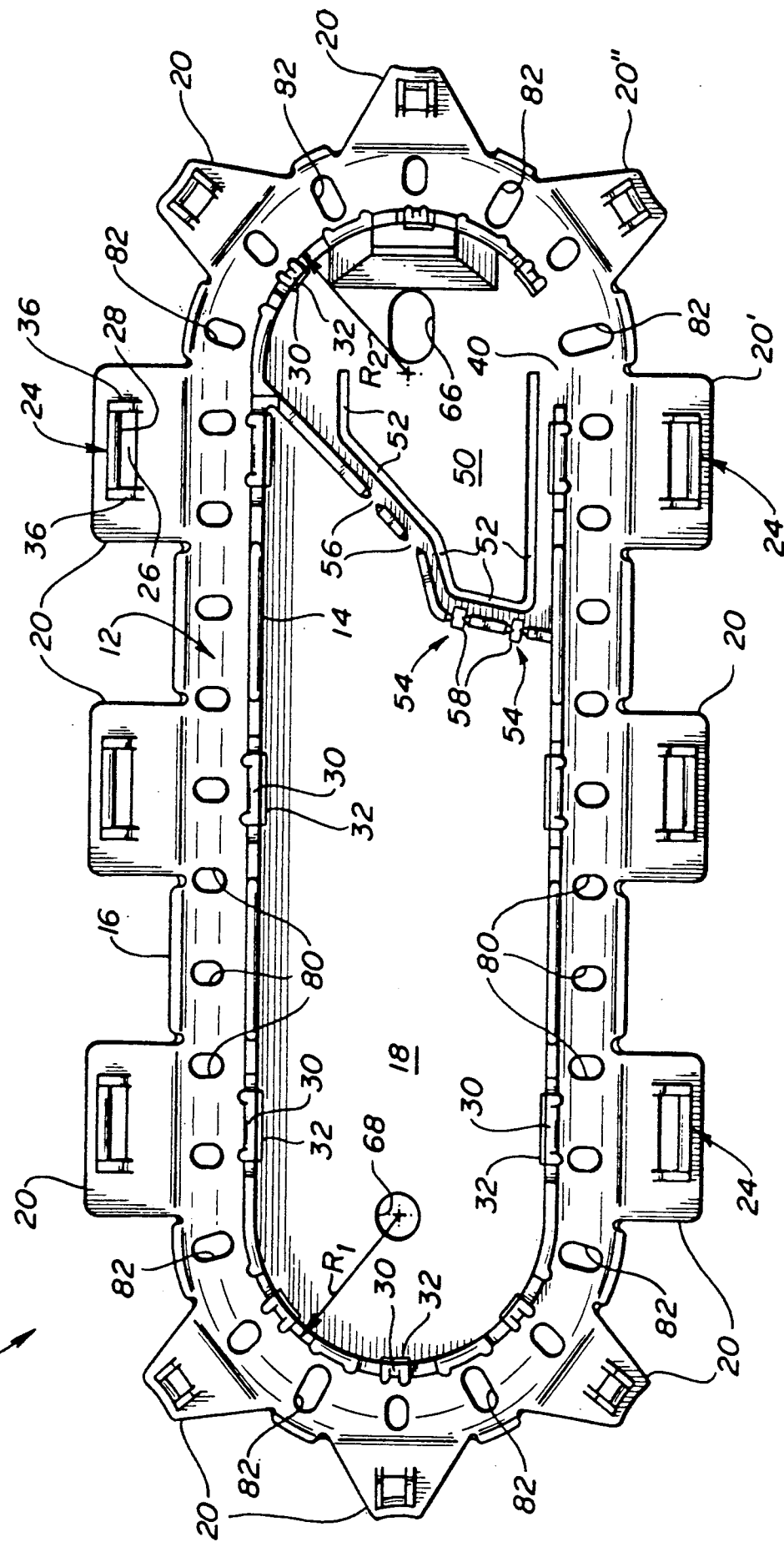
FIG. 1 is a plan view of a suture package of the prior art.

It is important that a suture package be designed so that the suture does not bind as it is removed from the package. In one type of suture package of the prior art, the suture is wound in an oval pattern and the suture is then retained in an oval-shaped open channel. The oval is generally symmetrical, with opposing straight sections joined at the ends by two semicircular sections of equal radius. Various embodiments of oval wrap suture packages have been disclosed, both one-piece (U.S. Pat. No. 4,967,902) and two-piece (U.S. Pat. No. 4,961,498) construction FIG. 1 depicts a plan view of a one-piece suture package of the prior art. The package 10 includes a central floor area 18 which is surrounded by an outer oval channel 12 having two opposing straight sections connected by two semicircular end sections. The end sections have radii $R_1$ and $R_2$, which are equal. The channel is defined by an inner wall 14 which entends upwardly from the floor area. Portions of the door locking means are formed at intervals about the inner wall 14. The bottom and outer periphery of the channel 12 is defined by a curved section 16 of the package, which extends outwardly from the inner wall 14 at the level of the floor 18 and curves upwardly to approximately the elevation of the inner wall 14. Attached at the outer periphery of the curved section 16 are a pluality of hinged doors 20. The doors are hinged at an elevation which is slightly below the uppermost elevation of the outer periphery of the curved section and the inner wall so that, when the doors are folded over the channel and latched in place, the upper surfaces of the doors will align with the upper elevation of the outer periphery and inner wall. Formed in each door is a portion of the door locking means 24, including a latch opening 26 bounded by a door latch projection 28 and two fins 36. When the door is closed over channel 12, the top of the latch post 30 engages the door latch opening 26 and the door latch projection 28 hooks around the latch post projection 32 to lock the door in the closed position.

Located inside the oval channel is an optional needle park including undercut and rigid needle holders 54 and 56. The package floor beneath needle holder 54 has been undercut by removal of the floor area indicated at 58, which enables the tapered ends of the overlying needle holder to flex and bend somewhat when a needle is inserted in the wall opening. Thus, the undercut needle holder 54 can accommodate a wider range of needle gauges than the rigid needle holder 56 can accommodate. Adjacent the needle park is a relief flap 50 defined by a cutout 52. A portion of the inner wall 14 is eliminated in the vicinity of the needle park to form a vent 40 in the channel wall through which the suture of the needle accesses the channel 12 between doors 20' and 20''.

The bottom of the channel 12 formed by the curved section 16 is periodically perforated by holes 80 and 82 around the circumference of the channel. These holes are used for assembling the package with a suture and, optionally, a needle, as follows: Package 10 is placed on an assembly platform that has a number of upwardly extending pins. Two of the pins are aligned to extend upward through holes 66 and 68 in the center of the package to retain the package in its assembly position on the platform. Eight other pins extend upward and are aligned to pass through the holes 82 of the channel. The platform is open beneath the remaining channel holes 80 and a vacuum source below the platform draws air through the holes 80. With the package so emplaced, the needle is located in the needle holder, and the suture is looped above the pin extending through hole 66 then downward through the vent 40 and into the channel. The suture is then wound in a clockwise direction around the pins which extend through the channel holes 82.

Additional details regarding the construction of the suture package of FIG. 1 appear in U.S. Pat. No. 4,967,902, incorporated herein by reference.

Although the suture package of FIG. 1 permits packaged sutures to be removed without binding in the great majority of instances, there are occasional problems of varying degree. A suture may bind as it is being removed from the package but will completely dispense if the tension on the suture is momentarily relaxed, a procedure called a "repull." More than one repull may be needed to completely dispense a suture. In some instances the suture either does not dispense from the tray at all, even after the tension is relaxed, or requires more than five repulls in order to dispense completely. Those instances are called "non-dispenses."

It has now been found that both repulls and non-dispenses can be substantially reduced by using oval wrap packages in which the radii of the two semicircular end sections are different.

Figure 2:
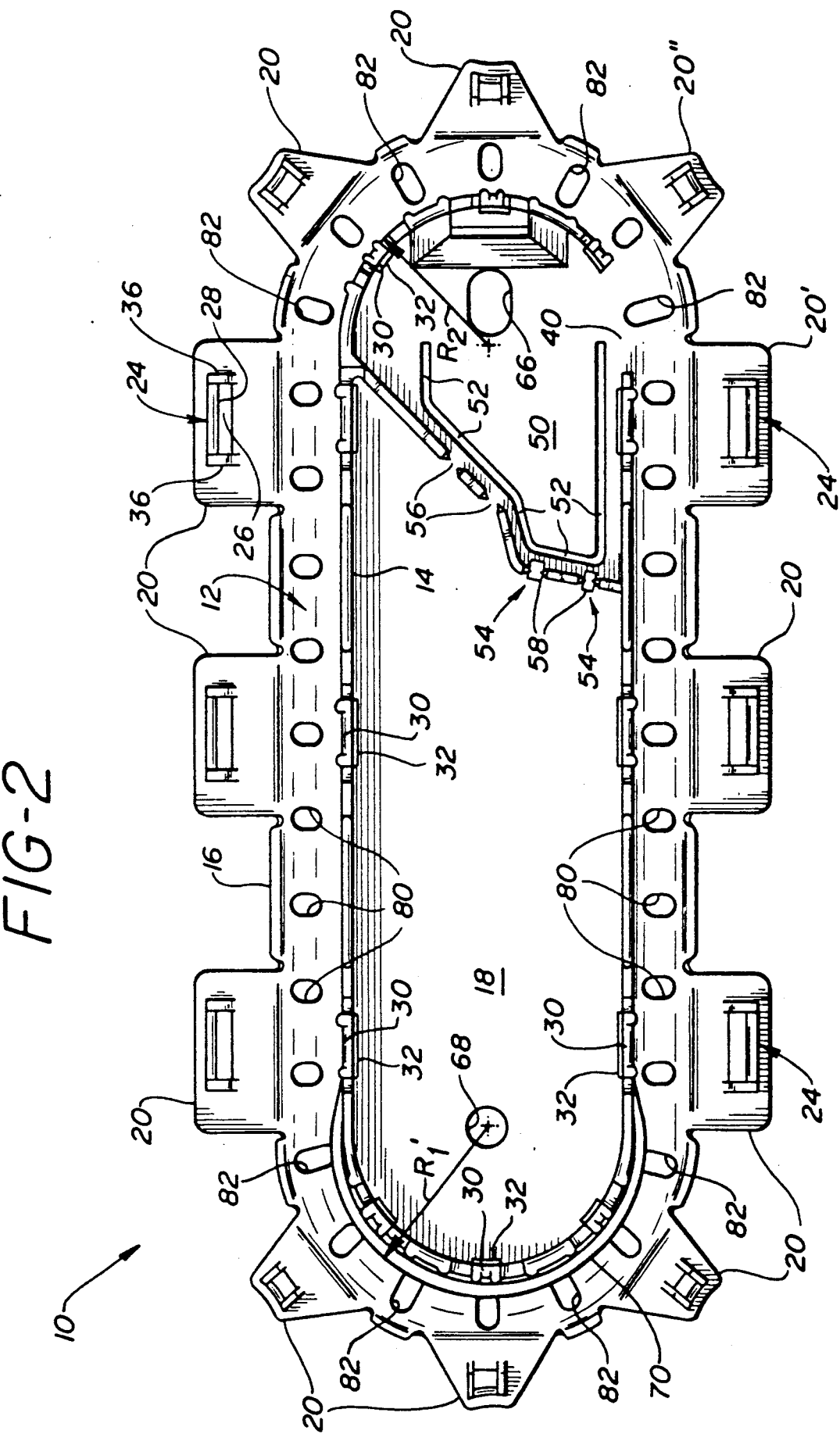
FIG. 2 is a plan view of a suture package of the present invention.

FIG. 2 is a plan view of a suture package of the present invention, in which reference numerals identify the same elements as they do in FIG. 1. Wall element 70 makes the radius $R_1'$ of an end section at one end of the oval greater than $R_2$, the radius of the opposing end section. Preferably, $R_1$ is at least about 5% larger than $R_2$. A limit on how large $R_1$ may be is set by the desire to maintain the (standard) outer dimension of the package. Since a loosely wound suture dispenses more easily, a looser winding is a trivial solution to the problem of binding; however, at some point looser winding becomes incompatible with compact packaging. The present invention optimizes the smooth dispensing capability of an oval wrap suture package having a given outer dimension. Although we have depicted the invention in the particular embodiment of FIG. 2, it is clear that any oval wrap suture package may be redesigned to embody the unequal radii of the present invention.

The mechanism by which sutures bind while being withdrawn from a package generally involves the "capstan effect," whereby the filament is bound against the inner wall of the channel. All sutures take a set; i.e., conform to the configuration in which they are held. Stiffer or springier sutures tend to spring to the outer wall of the channel and take a set that distances them from the inner wall. During dispensing, the spring and set keep the loops loose and away from the inner wall, excepting only the length that is being pulled out of the package. Monofilament and large-diameter sutures tend to be springy and are less likely to bind during dispensing. Braided multifilament suture is less springy and, therefore, provides more of a challenge to smooth dispensing. The problem is exacerbated by suture shrinkage during sterilization and/or heat sealing of the package. Shrinkage of braided sutures is typically in the range from about $\frac{1}{2}\%$ to 2%.

The package of the present invention apparently reduces the capstan effect. In an oval that has different radii over its end sections, the set taken by the suture at the large-radius end permits the suture loops to loosen as they pass around the small-radius end, reducing the tendency to bind. The dissimilar radii are particularly helpful to compensate for the lack of set, low springiness, and high shrinkage that characterize braided sutures.

The package depicted in FIG. 2 may be formed, preferably by molding, from any sterilizable thermoplastic material. Suitable materials include polyester, polyethylene, polyvinyl chloride, polypropylene, and polystyrene. Polypropylene is preferred, because it has good dimensional stability, in addition to its other well-known properties.

Another approach to ensuring that sutures can be dispensed without binding involves a lubricant coating, or "slip agent," on the surface of the thermoplastic material of the package. Suitable lubricants include oleamides, organosilicones, polytetrafluoroethylene, polydimethylsiloxane, polybutylate, ethoxylated lauryl alcohol, fatty acids, and mineral oil. Preferably, the lubricant is an oleamide; for example Kemamide* U, available from the Humko Division of Witco Chemical Co., Memphis, Tenn. Although the lubricant may be applied to the surface after the package is formed, the preferred procedure is to incorporate the lubricant in the material; for example, by molding a mixture of resins that includes the slip agent. The resin that incorporates the slip agent is incompatible with the base resin of the package material. As a result, the agent migrates to the surface of the molded package and provides the desired lubricity. Small amounts of slip agents have been incorporated into earlier suture packages, for example to facilitate doors 20 snapping closed onto latch posts 30. However, much higher concentrations (at least about 4 times as much) are used in the present package than were used in prior art packages. Preferably, if the slip agent is an oleamide, it comprises at least about 4% by weight of the total material. The maximum amount of oleamide that can be used is typically limited to about 12.5%, beyond which the mechanical properties of the molding suffer.

The present invention also includes an oval wrap suture package that is molded from a polymeric resin mixture, at least 4% of which comprises an oleamide. Such a suture package provides substantially improved dispensing characteristics, even if the end section radii are equal. Preferably such a suture package is molded from a resin mixture of polypropylene and oleamide resins, in which the oleamide is about 7.5% of the total.

EXAMPLE 1

Comparisons of the dispensability of three different oval wrap suture packages were made. The material of each package included 1% oleamide in polypropylene.
  A. The suture package of FIG. 1 (Prior Art).
  B. The suture package of FIG. 1, with the radius at one end increased by 8%.
  C. The suture package of FIG. 1, with the radius at both ends increased by 8%, compared to A. (Prior Art)

Coated Vicryl* Sutures of two sizes—0 and 3-0—were tested on each of the three package types. Sample size for each test was 400. The results are tabulated in Table 1, which shows that package B showed substantially better dispensability than did A or C.

TABLE 1

| Package | Non Dispense | Repulls |   |   |   |   |
|---|---|---|---|---|---|---|
|   |   | 1 | 2 | 3 | 4 | 5 |
| Size 0 Sutures |
| A | 2 | 9 | 2 | 3 | 0 | 1 |
| B | 0 | 2 | 2 | 0 | 0 | 0 |
| C | 2 | 14 | 4 | 2 | 2 | 2 |
| Size 3-0 Sutures |
| A | 2 | 20 | 12 | 10 | 7 | 0 |
| B | 0 | 8 | 6 | 0 | 0 | 0 |
| C | 3 | 14 | 6 | 3 | 0 | 1 |

EXAMPLE 2

Preparation of Suture Packages B' and C' of Example 3

An oval suture package was molded from a mixture of pellets, as follows:
85% polypropylene resin
15% 50/50 mixture of polyethylene and Kemamide* U resin After blending the resins with a ratio blender, the mix was liquefied in the barrel of a conventional injection molding machine at a temperature of about 500° F. (260° C.) and then injected under high pressure into an oval suture package mold having equal radii at both ends.

EXAMPLE 3

Comparisons of the dispensability of four different oval wrap suture packages were made:
  B. The same suture package as "B" of Example 1.
  B'. Suture package "B" of Example 1, except that the package material includes 7.5% oleamide.
  C. The same suture package as "C" of Example 1. (Prior Art)
  C'. Suture package "C" of Example 1, except that the package material includes 7.5% oleamide.

The sutures of Example 1 were tested with each of the four packages. Sample size for each test was 400. The results are tabulated in Table 2, which shows that increasing the oleamide content of the package material to 7.5% improves dispensability of "equal-radii" (i.e. prior art) suture packages.

TABLE 2

| Package | Non Dispense | Repulls |   |   |   |   |
|---|---|---|---|---|---|---|
|   |   | 1 | 2 | 3 | 4 | 5 |
| Size 0 Sutures |
| B | 0 | 2 | 2 | 0 | 0 | 0 |
| B' | 0 | 4 | 0 | 0 | 0 | 0 |
| C | 2 | 14 | 4 | 2 | 2 | 2 |
| C' | 0 | 11 | 4 | 0 | 0 | 0 |
| Size 3-0 Sutures |
| B | 0 | 8 | 6 | 0 | 0 | 0 |
| B' | 0 | 3 | 0 | 0 | 0 | 0 |
| C | 3 | 33 | 6 | 3 | 0 | 1 |
| C' | 0 | 17 | 2 | 1 | 1 | 0 |

We claim:
1. A suture package that defines an oval suture winding channel, comprising two substantially straight opposing sections connected by opposing first and second semicircular end sections, in which the first semicircular section has a larger radius than the second semicircular section.

2. The package of claim 1 in which the radius of the first semicircular section is at least about 5% larger than the radius of the second semicircular section.

3. The package of claim 1 in which the suture package comprises a molded thermoplastic material.

4. The package of claim 3 in which the thermoplastic material is selected from the group consisting of polyester, polyethylene, polyvinyl chloride, polypropylene and polystyrene.

5. The package of claim 4 in which the thermoplastic material is polypropylene.

6. The package of claim 3 in which the suture package further comprises a lubricant.

7. The package of claim 6 in which the lubricant is selected from a group consisting of an oleamide, an organosilicone compound, polytetrafluoroethylene; polymethylsiloxane, polybutylate, ethoxylated lauryl alcohol, a fatty acid, and mineral oil.

8. The package of claim 7 in which the lubricant is an oleamide.

9. The package of claim 8 in which the lubricant constitutes at least about 4% by weight of the package material.

10. The package of claim 6 in which the lubricant is a coating on the surface of the thermoplastic material.

11. The package of claim 6 in which the lubricant is incorporated in the thermoplastic material.

12. A suture package that defines an oval suture winding channel and that is molded from a polymeric resin mixture, at least 4% of which comprises an oleamide.

13. The package of claim 12 in which the package is molded from a mixture comprising polypropylene resin and about 7.5% oleamide resin.

* * * * *